United States Patent [19]

Srisathapat et al.

[11] Patent Number: 5,462,525
[45] Date of Patent: Oct. 31, 1995

[54] FLOW SENSOR FOR AN INFUSION PUMP

[75] Inventors: Chad Srisathapat, Sun Valley; Paul A. Yates, La Jolla, both of Calif.

[73] Assignee: MiniMed, Inc., a Delaware corporation, Sylmar, Calif.

[21] Appl. No.: 259,470

[22] Filed: Jun. 14, 1994

[51] Int. Cl.⁶ .................................................. A61M 5/00
[52] U.S. Cl. .................................................. 604/67
[58] Field of Search .................. 604/890.1, 891.1, 604/892.1, 30, 31, 50, 53, 65–67, 246, 247, 251, 253, 254; 128/DIG. 12, DIG. 13, 691–693; 200/81.9

[56] References Cited

U.S. PATENT DOCUMENTS

| | | |
|---|---|---|
| 754,496 | 3/1904 | Potter . |
| 1,292,334 | 1/1919 | Larsen . |
| 1,962,795 | 6/1934 | Walker . |
| 3,200,214 | 8/1965 | Aubert . |
| 3,330,269 | 7/1967 | Pieper .................................. 128/692 |
| 3,366,758 | 1/1968 | Bentzen et al. . |
| 3,368,045 | 2/1968 | Harper . |
| 3,440,374 | 4/1969 | Wintriss . |
| 3,766,779 | 10/1973 | Hoffman . |
| 4,373,527 | 2/1983 | Fischell . |
| 4,573,994 | 3/1986 | Rischell et al. . |
| 4,714,462 | 12/1987 | DiDomenico ......................... 604/891.1 |

Primary Examiner—C. Fred Rosenbaum
Assistant Examiner—Manuel Mendez
Attorney, Agent, or Firm—Kelly Bauersfeld & Lowry

[57] ABSTRACT

An infusion pump for delivering a selected medication to a patient is provided with an inductance flow sensor for monitoring and verifying delivery of medication in response to pump operation. The flow sensor comprises a compact inductor coil wrapped about a pump discharge conduit, in combination with a magnetically attractable core pin disposed within the discharge conduit for movement to a position within the inductor coil in response to pump outflow. A control circuit operates with minimal power requirements to monitor coil inductance changes as a result of core pin displacement to confirm medication delivery to the patient in response to pump operation. A magnet mounted at one end of the inductor coil draws and retains the core pin at a position retracted from the coil in the absence of pump outflow.

19 Claims, 3 Drawing Sheets

FLOW SENSOR FOR AN INFUSION PUMP

BACKGROUND OF THE INVENTION

This invention relates generally to medication infusion pumps particularly of the type for implantation directly into the body of a patient, and for programmed operation to deliver medication to the patient. More specifically, this invention relates to an improved implantable infusion pump having a relatively simple flow sensor operable with minimum power requirements to monitor and verify medication outflow to the patient in response to infusion pump operation.

Medication infusion pumps are generally known in the art for use in delivering a selected medication to a patient in a scheduled or preprogrammed manner. In recent years, such infusion pumps have been developed in compact form adapted for direct implantation into the body of a patient, and to deliver a specific medication such as insulin to the patient in discrete doses over an extended time period. An implanted infusion pump of this general type includes an internal medication chamber for receiving and storing a supply of the selected medication in liquid form, with the medication being subjected to a predetermined storage pressure to ensure accurate and repeatable delivery conditions through the use of a miniature dispensing pump and associated programmed control means. In many cases, the medication storage pressure is less than ambient body pressure to prevent undesired leakage of the medication from the medication chamber into the body of the patient, and thereby positively prevent accidental overdose during certain failure modes. For one illustrative example of an implanted medication infusion pump of this general type, see U.S. Pat. No. 4,573,994.

While such implantable infusion pumps have constituted a major step forward in reliable and convenient administration of certain medications, certain failure mode conditions may nevertheless occur wherein the desired medication is not in fact delivered to the patient. For example, the medication is typically delivered from the dispensing pump through a small bore catheter to a selected administration site within the body of the patient, but nondelivery of the medication can occur despite proper pump operation in the event that the catheter becomes clogged. Alternately, although rare, medication nondelivery can be the result of mechanical pump failure. In the past, implantable infusion pumps have not included satisfactory means for verifying or confirming actual medication outflow to the patient in response to infusion pump operation.

There exists, therefore, a significant need for an improved implantable infusion pump, particularly with respect to providing means for monitoring and verifying actual delivery of the selected medication to the patient in response to operation of the dispensing pump. The present invention fulfills these needs and provides further related advantages.

SUMMARY OF THE INVENTION

In accordance with the invention, a medication infusion pump for programmed administration of a selected medication to a patient is provided with a compact inductance flow sensor for monitoring and verifying medication outflow in response to pump operation. The flow sensor includes an inductor coil wrapped about a portion of a pump discharge conduit, in combination with a magnetically attractable core pin disposed along the discharge conduit for flow-responsive movement relative to the inductor coil. A control circuit responds to a low power input signal to monitor coil inductance changes attributable to core pin displacement to confirm and verify medication outflow as a result of pump operation.

The inductance flow sensor is particularly designed for integration into an infusion pump of the type adapted for direct implantation into the body of a patient. Such infusion pump includes an hermetically sealed housing with a medication chamber and miniature dispensing pump for delivering the medication in programmed doses from the chamber and through a pump discharge conduit to the patient. An electronic controller and associated battery power supply are also mounted within the housing for operating the pump on a programmed schedule over a prolonged time period. The flow sensor includes the inductor coil wrapped externally about the pump discharge conduit. The core pin is mounted directly within the discharge conduit for movement between a first position retracted axially from the inductor coil and a second position disposed coaxially within the coil. Medication outflow through the discharge conduit, as a result of infusion pump operation to dispense a medication dose to the patient, displaces the core pin to the second position and thereby alters the inductance of the surrounding coil. A magnet positioned outside the conduit and axially adjacent to the inductor coil draws and normally retains the core pin in the first position retracted from the coil.

The control circuit responds to operation of the infusion pump to connect a short duration and low power pulse to the inductor coil for monitoring inductance changes attributable to core pin movement. In the preferred form, the control circuit includes a pair of tuned oscillator circuits, one of which includes the flow sensor coil and the other being designed to match the inductance of the flow sensor coil during a selected position of the core pin, such as during a pump nonflow condition. The oscillator circuit outputs are compared to provide an indication of pump outflow or nonflow through the discharge conduit in response to pump operation. In the event of a nonflow condition, an alarm is activated and/or the pump controller is appropriately signaled for exterior telemetering of an indication of medication nondelivery.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF PREFERRED EMBODIMENT

Figure 1:
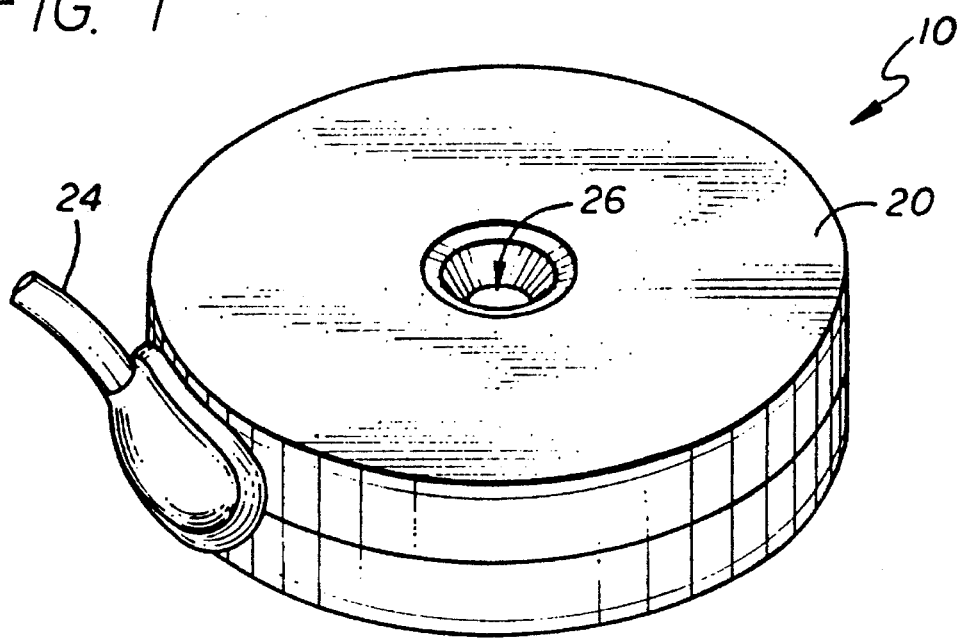
FIG. 1 is a perspective view of an implantable medication infusion pump adapted for implantation into the body of a patient, and further adapted to include the improved flow sensor embodying the novel features of the invention.
Figure 2:
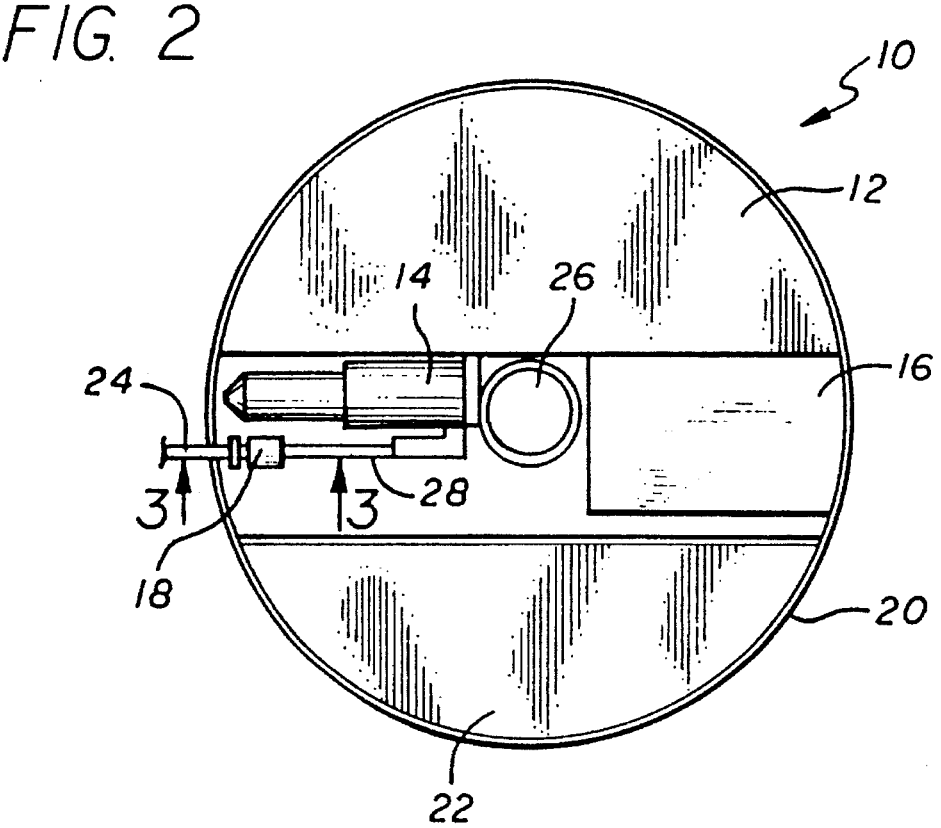
FIG. 2 is a top plan view of the implantable infusion pump of FIG. 1, with an upper portion of a pump housing removed to illustrate internal pump components in somewhat schematic form.

As shown in the exemplary drawings, an implantable medication infusion pump referred to generally in FIGS. 1 and 2 by the reference numeral 10 is provided for use in administering a selected medication to a patient in a controlled, preprogrammed manner. The infusion pump 10 receives and stores a quantity of a selected medication within an internal medication chamber 12. A small and preferably positive displacement dispensing pump 14 is operated by an electronic controller 16 to deliver the medication to the patient at prescribed times and in predetermined dosages. An inductance flow sensor 18 monitors actual medication outflow from the pump 14 to verify medication delivery to the patient in response to pump operation.

The illustrative medication infusion pump 10 comprises a small and substantially self-contained unit for direct implantation into the body of a patient. The pump 10 comprises an hermetically sealed pump housing 20 formed from a biocompatible material such as titanium or titanium alloy. The pump housing defines the internal medication chamber 12 for receiving and storing the supply of the selected medication in liquid form, such as insulin for a diabetic patient. The miniature dispensing pump 14 and associated electronic controller 16 are also mounted within the housing 20 in combination with a battery 22 for periodically operating the pump 14 to delivery medication to the patient via an appropriate catheter 24 or the like. The controller 16 is suitably preprogrammed to deliver the medication in accordance with individual patient need. An inlet or refill fitting 26 on the pump housing 20 is adapted to receive a hypodermic needle (not shown) to permit percutaneous refilling of the medication chamber 12 without requiring surgical access to the infusion pump 10. For a more detailed description of the overall construction and operation of implantable infusion pumps of this general type, see U.S. Pat. Nos. 4,373,527 and 4,573,994, which are incorporated by reference herein.

The inductance flow sensor 18 is mounted within the pump housing 20 at the discharge side of the dispensing pump 14. More particularly, as depicted in the illustrative embodiment (FIG. 2), the flow sensor 18 is mounted along a portion of a pump discharge conduit connected between the discharge side of the pump 14 and the catheter 24. The flow sensor 18 is designed to monitor actual flow of liquid medication through the discharge conduit and thereby permit confirmation that medication dispensing to the patient has occurred in response to a pump actuation signal or signals delivered from the controller 16 to the dispensing pump 14. Alternatively, the flow sensor 18 will detect and indicate a nonflow condition through the pump discharge conduit for purposes of indicating medication nondelivery.

Figure 3:
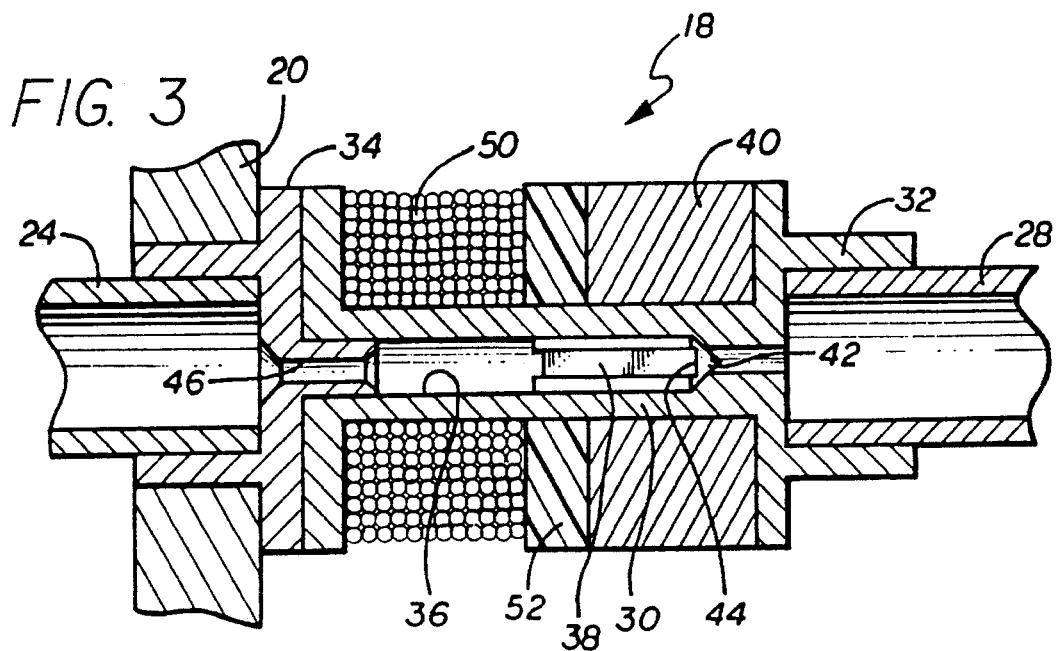
FIG. 3 is an enlarged fragmented sectional view of the flow sensor, taken generally on the line 3—3 of FIG. 2, and depicting the flow sensor in a nonflow condition.
Figure 4:
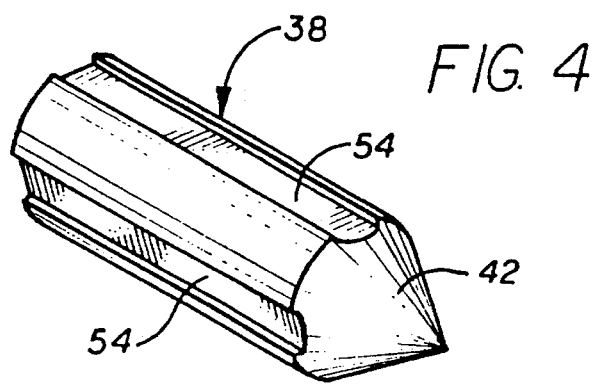
FIG. 4 is an enlarged perspective view illustrating one preferred form of a core pin for use in the flow sensor of FIG. 3.

As shown in FIG. 3, the preferred flow sensor 18 comprises a short tubular segment 30 of a biocompatible material such as titanium and having an appropriate fitting 32 at an upstream end thereof for in-line connection with a pump discharge tube 28, with the discharge tube 28 and the tubular segment 30 cooperatively defining the pump discharge conduit. An opposite or downstream end of the tubular flow sensor segment 30 is adapted for in-line connection with a wall fitting 34 on the housing 20 for interconnecting the flow sensor 18 with the patient delivery catheter 24. A central bore 36 formed in the tubular segment 30 is thus connected in-line between the pump discharge tube 28 and the catheter 24 for flow-through passage of the medication administered to the patient.

A core pin 38 of a magnetically attactable or permeable material is positioned within the central bore 36 of the flow sensor segment 30, wherein the core pin is designed for back-and-forth displacement within the tubular segment 30 in response to medication flow or nonflow. More specifically, a ring magnet 40 mounted externally about an upstream end region of the tubular segment 30 magnetically attracts and draws the core pin toward a first or normal position generally at an upstream end of the bore 36. A conically tapered nose 42 on the upstream end of the core pin engages a conical seat 44 formed along the bore 36 to define an upstream end stop. Similarly, the wall fitting 34 at the downstream end of the tubular segment 30 includes a short tubular nipple 46 protruding into the downstream end of the bore 36 to define a downstream end stop to core pin movement, as will be described.

Figure 5:
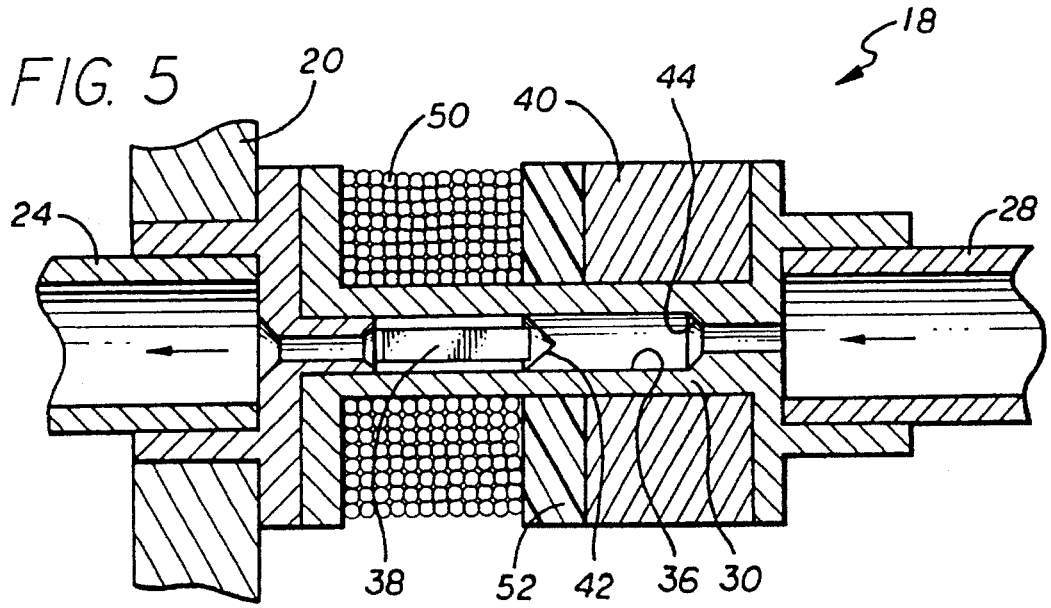
FIG. 5 is an enlarged fragmented sectional view similar to FIG. 3, and illustrating the flow sensor during a fluid flow condition.

During a nonflow condition as illustrated in FIG. 3, the ring magnet 40 draws the core pin 38 longitudinally along the bore 36 generally to the upstream end of the flow sensor in engagement with the stop seat 44. However, when liquid medication is discharged from the dispensing pump 14 for flow-through passage through the flow sensor 18, the medication flow physically contacts and displaces the core pin 38 toward a downstream position with its tail end contacting the downstream end stop 46, as viewed in FIG. 5. In this latter position, the core pin 38 is displaced away from its normal position generally coaxially within the ring magnet 40, to a second, flow-indicative position generally coaxially within an inductor coil 50 wrapped about the exterior of the tubular segment 30 at a downstream region thereof. As a result, the inductance associated with the inductor coil 50 changes from a low inductance associated with medication at the coil core, to a much higher inductance as the core pin 38 occupies the core region of the inductor coil. When the medication flow ceases, the magnet 40 draws the core pin 38 back to the upstream position, whereby the coil inductance decreases as the core pin leaves the core region thereof. An insulator disk 52 is conveniently interposed axially between the magnet 40 and the inductor coil 50 to isolate the magnetic flux fields associated therewith.

During normal operation of the dispensing pump 14, the medication is administered to the patient in discrete positive displacement pulses, several of which may occur within a time period of several minutes and collectively constitute a dose of medication administered to the patient. Each medication flow pulse is directed against the tapered nose end 42 of the core pin 38 for unseating and displacing the core pin toward the downstream position within the inductor coil 50. In a typical implantable infusion pump, the medication flow pulse is a small increment on the order of one-half microliter, with the preferred flow sensor including a bore size and core pin geometry for core pin displacement substantially to the second position within the coil in response to a flow pulse of this magnitude. Longitudinal channels 54 may be formed in the exterior of the core pin 38 to facilitate medication bypass flow to the catheter 24, although such bypass flow may be obtained by selecting appropriate clearance dimensions between the core pin and the bore 36.

Figure 6:
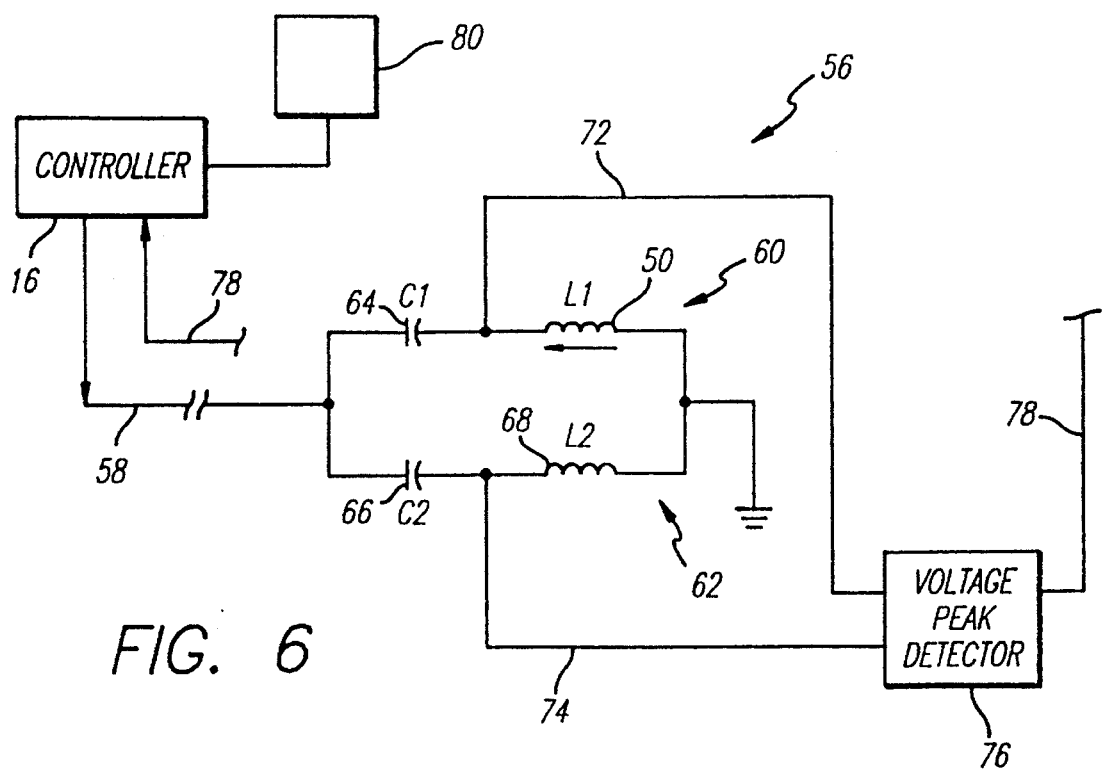
FIG. 6 is a schematic circuit diagram illustrating one preferred control circuit for use in conjunction with flow sensor of FIG. 3.

Inductance changes associated with the coil 50 are monitored by a control circuit 56 shown in FIG. 6. In particular, the control circuit 56 receives an input voltage of short duration from the controller 16 via an input line 58. This input pulse, which can have an extremely short pulse duration on the order of one microsecond to minimize power consumption, is delivered to the control circuit 56 at a predetermined point in time following operation of the dispensing pump 14 by a few seconds, wherein the timing of the input pulse is correlated with core pin displacement to the downstream position upon proper discharge flow of medication from the pump. The input pulse is applied to a parallel pair of oscillator circuits 60 and 62 tuned to substantially the same frequency. The oscillator circuit 60 includes a capacitor 64 and the inductor coil 50 of the flow sensor 18 mounted along the pump discharge conduit. The second oscillator circuit 62 includes a capacitor 66 and inductor coil 68 designed so that the two oscillator circuits are tuned to substantially the same frequency during a known condition of the flow sensor, such as the nonflow condition with the core pin 38 retracted to within the magnet 40.

Figure 7:
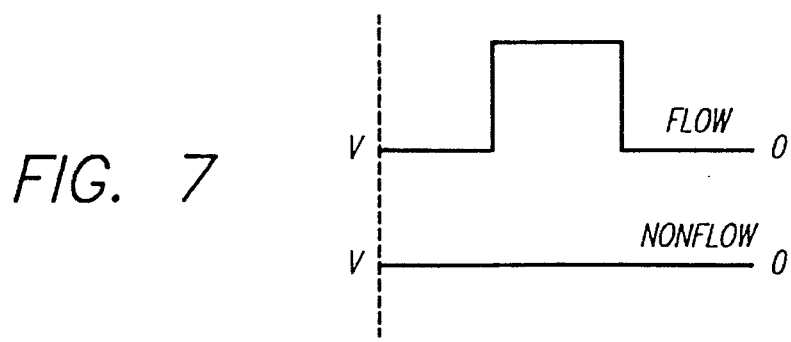
FIG. 7 is a graphic representation of output voltages obtained from the control circuit of FIG. 6 during flow and nonflow conditions, respectively.

Voltage outputs from the oscillator circuits 60 and 62 in response to the input pulse on line 58 are respectively connected via lines 72 and 74 to a peak voltage detector 76. When these voltage outputs of the oscillator circuits are substantially identical, as represented by the nonflow condition, an output on line 78 from the voltage peak detector 76 is essentially zero, as indicated in FIG. 7. Conversely, when the core pin 38 has moved to the downstream position within the inductor coil 50 to alter the inductance associated therewith, the voltage outputs from the oscillator circuits 60 and 62 are substantially different, resulting in a discrete output pulse from the peak detector 76 on line 78.

The output from the control circuit 56 is connected back to the electronic controller 16 for the infusion pump 10 for purposes of confirming proper medication dispensing in response to pump operation. In the event that a nonflow condition is detected by the control circuit 56, the controller 16 is appropriately signaled to indicate a malfunction. Such nondelivery of the medication is typically the result of a blocked catheter 24 or an empty medication chamber 12, such that appropriate remedial action can often be taken to resume normal medication delivery without requiring pump removal or surgical access thereto. On occasion, however, the nondelivery condition may be attributable to mechanical pump failure. In any case, the malfunction information supplied to the controller 16 can be used to activate an appropriate alarm 80, such as an audio alarm or internal tickle alarm of a type known in the art. Alternately, the controller 16 may store the nonflow information pending periodic telemetering of program information via appropriate radio signals to an external programming device.

In accordance with one further aspect of the invention, the magnet 40 and the core pin 38 are desirably designed to provide a predetermined magnetic force applied to the core pin for normally retaining the core pin in the first position (FIG. 3) with its nose end 42 seated on the seat 44. That is, in implantable infusion pumps of the type shown and described herein, the medication chamber 12 within the pump housing 20 is normally maintained at a selected and substantially constant pressure to insure delivery of accurate and repeatable medication doses. This constant pressure is usually a slight negative pressure to prevent medication leakage from the housing 20 into the patient during certain failure mode conditions. However, the negative pressure level is altitude dependent, such that the actual pressure applied to the medication chamber typically reaches a zero gauge pressure at an elevation of several thousand feet above sea level. By magnetically retaining the core pin 38 against the seat 44 with a predetermined magnetic attraction force, such as about one psi, the core pin 38 effectively provides a safety valve to prevent medication leakage at high altitudes. The low magnetic retention force, however, is easily overcome by medication discharge upon proper pump operation for core pin displacement to within the inductor coil 50, as previously described.

Figure 8:
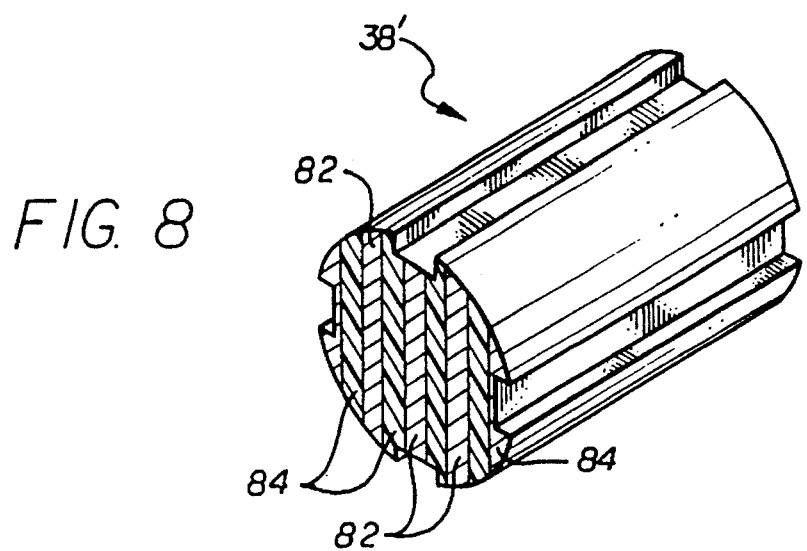
FIG. 8 is an enlarged cross sectional view depicting an alternative core pin construction for use with the invention.

FIG. 8 illustrates an alternative core pin construction, wherein a modified core pin 38' is shown to include a plurality of alternating layers of metal 82 and plastic 84. With this modified construction, the core pin 38' is formed from a reduced proportion of magnetically attachable material. This pin construction beneficially provides the necessary inductance changes for flow sensor operation, while reducing eddy currents to an insignificant level. In this regard, although FIG. 8 depicts laminated layers of magnetically attractable and insulative material, it will be understood that a variety of combination metal and plastic or similar materials can be used to form the core pin.

The flow sensor 18 thus monitors and verifies actual medication outflow from the dispensing pump 14 in response to a pump operation to ensure that medication is actually delivered to the patient. In the event that a nonflow condition is detected, the control circuit 56 associated with the flow sensor is adapted to activate an appropriate alarm or otherwise provide an indication of the medication nondelivery, so that appropriate remedial action can be taken. This flow sensing function occurs with very low consumption of electrical power to thereby conserve the battery power supply 22, and further without requiring direct contact between the discharged medication and any electrical wires or related components.

A variety of further modifications and improvements to the invention described herein will be apparent to those skilled in the art. Accordingly, no limitation on the invention is intended by way of the foregoing description and accompanying drawings, except as set forth in the appended claims.

What is claimed is:

1. A medication infusion pump, comprising:

a pump housing having a medication chamber formed therein for receiving a supply of a selected medication;

pump means within said housing for delivering the medication from said medication chamber through a discharge conduit to a patient; and flow sensor means for monitoring flow of the medication through said discharge conduit, said flow sensor means including an inductor coil mounted externally about said discharge conduit, and a core pin of a magnetically attractable material mounted within said discharge conduit for displacement therein relative to said inductor coil in response to medication flow through said discharge conduit;

said flow sensor means including means for normally retaining said core pin in a first position retracted from said inductor coil during nonflow of medication through said discharge conduit, said core pin responding to flow of medication through said discharge conduit for displacement from said first position to a second position disposed generally coaxially within said inductor coil;

said core pin retaining means comprising means for magnetically retracting said core pin to said first position.

2. The medication infusion pump of claim 1 further including circuit means including said inductor coil for monitoring inductance changes associated with said inductor coil in response to core pin displacement relative to said inductor coil.

3. The medication infusion pump of claim 2 wherein said circuit means comprises a first oscillator circuit including said inductor coil, a second oscillator circuit tuned to substantially match said first oscillator circuit when said core pin is in a predetermined position relative to said inductor coil, means for supplying an input signal to said first and second oscillator circuits in response to intended operation of said pump means to deliver medication to a patient, and means for comparing the outputs of said first and second oscillator circuits.

4. The medication infusion pump of claim 3 wherein said predetermined core pin position is a position substantially retracted from said inductor coil and corresponding with a medication nonflow condition through said discharge conduit.

5. The medication infusion pump of claim 3 wherein said circuit means further includes an alarm for indicating medication nonflow through said discharge conduit in response to intended operation of said pump means.

6. The medication infusion pump of claim 1 wherein said discharge conduit defines a stop seat for retaining said core pin normally in said first position, said means for magnetically retracting said core pin normally retaining said core pin seated against said stop seat with a predetermined magnetic force.

7. The medication infusion pump of claim 1 wherein said magnetically retracting means comprises a ring magnet mounted externally about said discharge conduit at a position generally axially adjacent to said inductor coil.

8. The medication infusion pump of claim 7 further including an insulator disk disposed axially between said inductor coil and said ring magnet.

9. The medication infusion pump of claim 1 wherein said core pin cooperates with said discharge conduit to permit flow of medication through said discharge conduit and past said core pin for flow to a patient.

10. The medication infusion pump of claim 9 wherein said core pin has at least one longitudinally open flow channel formed therein.

11. The medication infusion pump of claim 1 wherein said core pin is formed from a combination of magnetically permeable and insulative materials.

12. A flow sensor for monitoring and verifying actual flow of a medication from a medication dispensing pump through a pump discharge conduit for delivery to a patient, said flow sensor comprising:

an inductor coil mounted about the pump discharge conduit;

a core pin of a magnetically attractable material mounted along the pump discharge conduit;

means forming first and second generally opposed end stops along the pump discharge conduit for limiting movement of said core pin along the conduit between a first position generally retracted from said inductor coil and a second position generally coaxially within said inductor coil; and retraction means for normally drawing and retaining said core pin at said first position, said core pin responding to medication flow through the pump discharge conduit for movement to said second position for the duration of said flow, said core pin cooperating with the pump discharge conduit to permit medication flow through the conduit and past the core pin;

said retraction means comprising a magnet mounted along the pump discharge conduit at a position generally axially adjacent to said inductor coil.

13. The flow sensor of claim 12 wherein said magnet and said inductor coil are mounted externally about the pump discharge conduit.

14. The flow sensor of claim 12 further including circuit means including said inductor coil for monitoring inductance changes associated with said inductor coil in response to core pin displacement between said first and second positions.

15. An inductance flow sensor for monitoring and verifying fluid flow through a flow passage, said flow sensor comprising:

a generally tubular member adapted for in-line connection with the flow passage for flow of the fluid therethrough;

a core pin of a magnetically attractable material mounted within said tubular member for movement therein between a first position seated against a first end stop defined by said tubular member, and a second position spaced from said first end stop;

an inductor coil mounted externally about said tubular member at a position with said core pin generally retracted axially therefrom when said core pin is in said first position, and with said core pin disposed generally coaxially therein when said core pin is in said second position; and retraction means for magnetically drawing and retaining said core pin in said first position during nonflow of the fluid through said tubular member, said core pin being displaced upon flow of the fluid through said tubular member to said second position, said core pin cooperating with said tubular member to permit fluid flow therethrough past said core pin when said core pin is spaced from said first end stop.

16. The flow sensor of claim 15 wherein said tubular member further includes a second end stop for engagement by said core pin when said core pin is in said second position.

17. The flow sensor of claim 15 further including circuit means including said inductor coil for monitoring inductance changes associated with said inductor coil in response to core pin displacement between said first and second positions.

18. The flow sensor of claim 17 wherein said circuit means comprises a first oscillator circuit including said inductor coil, a second oscillator circuit turned to substantially match said first oscillator circuit when said core pin is in a selected one of said first and second positions, and means for comparing the outputs of said first and second oscillator circuits.

19. The flow sensor of claim 15 wherein said core pin cooperates with said first end stop to substantially prevent fluid flow through said tubular member when said core pin is in said first position, said retraction means normally retaining said core pin seated against said first end stop with a predetermined force.

* * * * *